(12) United States Patent
Kristen et al.

(10) Patent No.: US 6,743,932 B2
(45) Date of Patent: Jun. 1, 2004

(54) POLYMERIZATION CATALYST

(75) Inventors: Marc Oliver Kristen, Limburgerhof (DE); Benno Bildstein, Innsbruck (AT); Michael Malaun, Wenns (AT); Ulrich Siemeling, Bielefeld (DE); Oliver Kuhnert, Bielefeld (DE)

(73) Assignee: Basell Polyolefine GmbH, Wesseling (DE)

( * ) Notice: Subject to any disclaimer, the term of this patent is extended or adjusted under 35 U.S.C. 154(b) by 469 days.

(21) Appl. No.: 09/827,099

(22) Filed: Apr. 6, 2001

(65) Prior Publication Data

US 2002/0016256 A1 Feb. 7, 2002

(30) Foreign Application Priority Data

Apr. 7, 2000 (DE) .......................... 100 17 430

(51) Int. Cl.$^7$ .......................... C07F 17/00; C07F 19/00; B01J 31/00
(52) U.S. Cl. .............................. 556/28; 556/9; 556/11; 556/16; 556/20; 526/127; 526/160; 526/352; 526/943; 502/103; 502/117; 502/120
(58) Field of Search ................................ 556/20, 9, 11, 556/12, 28, 14, 16; 502/103, 117, 120; 526/127, 160, 943, 352

(56) References Cited

U.S. PATENT DOCUMENTS

| | | | | |
|---|---|---|---|---|
| 4,404,344 A | | 9/1983 | Sinn et al. .................. 526/160 |
| 5,770,752 A | | 6/1998 | Kaufmann et al. ............ 556/11 |
| 5,892,081 A | | 4/1999 | Sueling et al. ................ 556/28 |
| 5,912,373 A | | 6/1999 | Fischer et al. ................. 556/7 |
| 6,043,363 A | * | 3/2000 | LaPointe et al. ............. 544/225 |
| 6,169,192 B1 | * | 1/2001 | Pugin et al. ................... 556/11 |
| 6,191,284 B1 | * | 2/2001 | Knochel et al. ............. 548/402 |

FOREIGN PATENT DOCUMENTS

| | | |
|---|---|---|
| DE | 30 07 725 | 9/1981 |
| DE | 195 47 247 | 6/1997 |
| EP | 0 468 537 | 1/1992 |
| EP | 763 044 | 3/1997 |
| EP | 854 876 | 7/1998 |
| EP | 0 891 980 | 1/1999 |
| WO | WO 95/32979 | 12/1995 |
| WO | WO 96/23010 | 8/1996 |
| WO | WO 97/03080 | 1/1997 |
| WO | WO 97/49712 | 12/1997 |
| WO | 837 865 | 4/1998 |
| WO | WO 98/27124 | 6/1998 |

OTHER PUBLICATIONS

C. Averbuj, et al., J. Am. Chem. Soc., vol. 120, No. 34, pp. 8640–8646, "Stereoregular Polymerization of α–Olefins Catalyzed by Chiral Group 4 Benzamidinate Complexes of $C_1$ and $C_3$ Symmetry", 1998.

(List continued on next page.)

Primary Examiner—Porfirio Nazario-Gonzalez
(74) Attorney, Agent, or Firm—Keil & Weinkauf

(57) ABSTRACT

An organometallic compound of the formula I

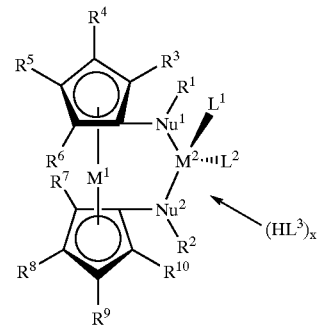

where $M^1$ is selected from among Fe, Ru and Os and $M^2$ is selected from among the transition metals of groups IV to VI of the Periodic Table, which can be prepared by reacting an organometallic compound of the formula II

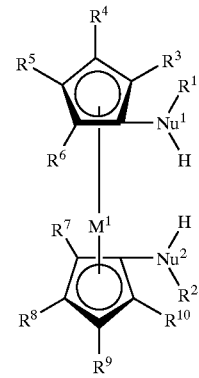

with a transition metal compound of the formula III, $$M^2L^1L^2(L^3)_{x+1} \quad\quad III$$

where the variables are as defined above and the organometallic compound of the formula II can, if desired, be doubly deproteinated beforehand, can be used as part of a catalyst system for the polymerization or copolymerization of olefins. This catalyst system comprises one or more organometallic compounds of the formula I and at least one activator. The compound of the formula I can also be used to produce a solid catalyst comprising at least one organometallic compound of the formula I, at least one activator and a solid support by impregnating a support material with one or more organometallic compounds of the formula I and at least one activator. This solid catalyst can be used in a process for the polymerization or copolymerization of olefins in bulk, in suspension or in the gas phase.

7 Claims, No Drawings

OTHER PUBLICATIONS

A. R. Barron, Macromol. Symp., vol. 97, pp. 15–25, "A New Understanding of the Co–Catalytic Activity of Alumoxanes: The Opening of a Black Box", 1995.

H. H. Brintzinger, et al. Angew. Chem. Int. Ed. Engl., vol. 34, pp. 1143–1170, "Stereospecific Olefin Polymerization with Chiral Metallocene Catalysts", 1995.

G. J. P. Britovsek, et al., Angew. Chem. Int. Ed., vol. 38, pp. 428–447, "The Search for New–Generation Olefin Polymerization Catalysts: Life Beyond Metallocenes", 1999.

G. J. P. Britovsek, et al., Angew Chem., vol. 111, pp. 449–468, "Auf Der Suche Nach Einer Neuen Generation Von Katalysatoren Zur Olefinpolymerisation: "Leben" Jenseits Der Metallocene", 1999.

G. M. Diamond, et al., Organometallics, vol. 15, No. 19, pp. 4030–4037, "Synthesis of Group 4 Metal Rac–(E-BI)M(NR$_2$)$_2$ Complexes by Amine Elimination. Scope and Limitations", 1996.

V. C. Gibson, et al., Chem. Commun., pp. 313–314, "High Activity Ethylene Polymerisation Catalysts Based on Chelating Diamide Ligands", 1998.

M. Herberhold, et al., Journal of Organometallic Chemistry, vol. 241, pp. 227–231 and 234–240, "Ferrocenylamine", 1983.

Y. Koide, et al., Organometallics, vol. 15, No. 9, pp. 2213–2226, "Alumoxanes as Cocatalysts in the Palladium–Catalyzed Copolymerization of Carbon Monoxide and Ethylene: Genesis of a Structure—Activity Relationship", 1996.

R. F. Kovar, et al., Organometallics Chemical Synthesis, vol. 1, pp. 173–181, "A Convenient Route to 1,1'–Dihalogenated Ferrocenes", 1970/1971.

H. Mack, et al., Journal of Organometallic Chemistry, vol. 525, pp. 81–87, "Synthesis, Characterization and Reactivity of Amido Titanium and Zirconium Complexes", 1996.

N. A. H. Male, et al., J. Chem. Soc., Dalton Trans., pp. 2487–2494, "Synthesis and Structue of Zirconium(IV) Alkyl Complexes with Bi–, Tri–, Tetra– and Penta–Dentate Amido Ligands", 1997.

A. Spannenberg, et al., Zeitschrift Fuer Anorganische Und Allgemeine Chemie, vol. 623, pp. 389–393, "Ferrocene Based Amido "Ligands"; Synthesis of Bimetallic Bis(Aminopyridinato) Titanium Complexes", 1997.

X. Yang, et al., J. Am. Chem. Soc., vol. 113, No. 9, pp. 3623–3625, "Cation–Like" Homogeneous Olefin Polymerization Catalysts Based Upon Zirconocene Alkyls and Tris(Pentafluorophenyl)Borane, 1991.

* cited by examiner

POLYMERIZATION CATALYST

The present invention relates to an organometallic compound of the formula I,

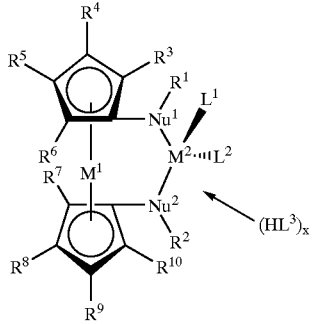

where the variables are defined as follows:
- $M^1$ is selected from among Fe, Co, Ru and Os,
- $M^2$ is a transition metal of group 4, 5 or 6 of the Periodic Table of the Elements,
- $Nu^1$ and $Nu^2$ are identical or different and are selected from among N, P and As,
- $R^1$ and $R^2$ are identical or different and are selected from among
  - $C_1$–$C_8$-alkyl, substituted or unsubstituted,
  - $C_3$–$C_{12}$-cycloalkyl, substituted or unsubstituted,
  - $C_7$–$C_{13}$-aralkyl,
  - $C_6$–$C_{14}$-aryl, unsubstituted or substituted by one or more identical or different substituents selected from among
    - $C_1$–$C_8$-alkyl, substituted or unsubstituted,
    - $C_3$–$C_{12}$-cycloalkyl,
    - $C_7$–$C_{13}$-aralkyl,
    - $C_6$–$C_{14}$-aryl,
    - halogen,
    - $C_1$–$C_6$-alkoxy,
    - $C_6$–$C_{14}$-aryloxy,
    - $SiR^{11}R^{12}R^{13}$ and $O$—$SiR^{11}R^{12}R^{13}$, where $R^{11}$–$R^{13}$ are selected from among $C_1$–$C_8$-alkyl, $C_3$–$C_{12}$-cycloalkyl, $C_7$–$C_{13}$-aralkyl and $C_6$–$C_{14}$-aryl;
  - five- to six-membered nitrogen-containing heteroaryl radicals, unsubstituted or substituted by one or more identical or different substituents selected from among
    - $C_1$–$C_8$-alkyl, substituted or unsubstituted,
    - $C_3$–$C_{12}$-cycloalkyl,
    - $C_7$–$C_{13}$-aralkyl,
    - $C_6$–$C_{14}$-aryl,
    - halogen,
    - $C_1$–$C_6$-alkoxy,
    - $C_6$–$C_{14}$-aryloxy,
    - $SiR^{11}R^{12}R^{13}$ and $O$—$SiR^{11}R^{12}R^{13}$, where $R^{11}$–$R^{13}$ are selected from among $C_1$–$C_8$-alkyl, $C_3$–$C_{12}$-cycloalkyl, $C_7$–$C_{13}$-aralkyl and $C_6$–$C_{14}$-aryl;
- $R^3$ to $R^{10}$ are hydrogen,
  - $C_1$–$C_8$-alkyl, substituted or unsubstituted,
  - $C_3$–$C_{12}$-cycloalkyl, substituted or unsubstituted,
  - $NO_2$,
  - halogen,
  - $C_7$–$C_{13}$-aralkyl,
  - $C_6$–$C_{14}$-aryl, unsubstituted or substituted by one or more identical or different substituents selected from among
    - $C_1$–$C_8$-alkyl, substituted or unsubstituted,
    - $C_3$–$C_{12}$-cycloalkyl,
    - $C_7$–$C_{13}$-aralkyl,
    - $C_6$–$C_{14}$-aryl,
    - halogen,
    - $C_1$–$C_6$-alkoxy,
    - $C_6$–$C_{14}$-aryloxy,
    - $SiR^{11}R^{12}R^{13}$ and $O$—$SiR^{11}R^{12}R^{13}$, where $R^{11}$–$R^{13}$ are selected from among $C_1$–$C_8$-alkyl, $C_3$–$C_{12}$-cycloalkyl, $C_7$–$C_{13}$-aralkyl and $C_6$–$C_{14}$-aryl;
  - five- to six-membered nitrogen-containing heteroaryl radicals, unsubstituted or substituted by one or more identical or different substituents selected from among
    - $C_1$–$C_8$-alkyl, substituted or unsubstituted,
    - $C_3$–$C_{12}$-cycloalkyl,
    - $C_7$–$C_{13}$-aralkyl,
    - $C_6$–$C_{14}$-aryl,
    - halogen,
    - $C_1$–$C_6$-alkoxy,
    - $C_6$–$C_{14}$-aryloxy,
    - $SiR^{11}R^{12}R^{13}$ and $O$—$SiR^{11}R^{12}R^{13}$, where $R^{11}$–$R^{13}$ are selected from among $C_1$–$C_8$-alkyl, $C_3$–$C_{12}$-cycloalkyl, $C_7$–$C_{13}$-aralkyl and $C_6$–$C_{14}$-aryl;
  - where in each case two adjacent radicals $R^3$ to $R^6$ or $R^7$ to $R^{10}$ together with the C atoms of the parent aromatic may form a 5- to 8-membered ring or sterically favorably positioned radicals may form a bridge between the two $C_5$ rings;
- $L^1$ to $L^3$ are identical or different and are selected from among
  - $NR^{14}R^{15}$, where $R^{14}$ and $R^{15}$ are identical or different and are selected from among $C_1$–$C_8$-alkyl, $C_3$–$C_{12}$-cycloalkyl, $C_2$–$C_8$-alkenyl having one or more conjugated or nonconjugated double bonds, $C_7$–$C_{13}$-aralkyl, $C_6$–$C_{14}$-aryl, $SiR^{11}R^{12}R^{13}$ and $O$—$SiR^{11}R^{12}R^{13}$, where $R^{11}$–$R^{13}$ are selected from among $C_1$–$C_8$-alkyl, $C_3$–$C_{12}$-cycloalkyl, $C_7$–$C_{13}$-aralkyl and $C_6$–$C_{14}$-aryl; and where $R^{14}$ and $R^{15}$ together with N may form a five- to ten-membered, saturated or unsaturated ring which may in turn be substituted by $C_1$–$C_6$-alkyl,
  - halide,
  - $C_1$–$C_8$-alkyl, substituted or unsubstituted,
  - $C_3$–$C_{12}$-cycloalkyl,
  - $C_7$–$C_{13}$-aralkyl,
  - $C_6$–$C_{14}$-aryl,
  - $C_1$–$C_6$-alkoxy;
  - $C_6$–$C_{14}$-aryloxy,
- x is an integer from 0 to 3.

The present invention further provides a process for preparing a compound of the formula I, which comprises reacting an organometallic compound of the formula II with a transition metal compound of the formula III

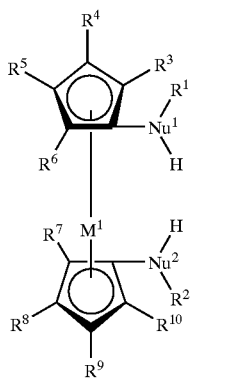

II

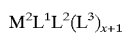   III where the variables are as defined above. In this reaction, the organometallic compound of the formula II may, if desired, be doubly deproteinated beforehand. The invention also provides an organometallic compound of the formula II.

Furthermore, the present invention provides a process for preparing an organometallic compound II by reacting an organometallic compound of the formula IV

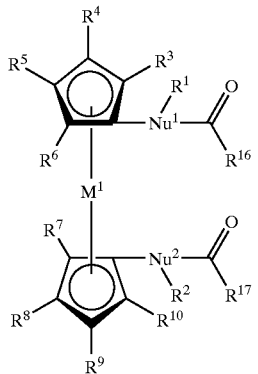

IV with a hydroxide compound $M^3OH$ or $M^4(OH)_2$, where $M^3$ is Li, Na, K, Rb or Cs and $M^4$ is Mg, Ca, Sr or Ba and $R^{16}$ and $R^{17}$ are selected independently from among $C_1$–$C_8$-alkyl, $C_3$–$C_{12}$-cycloalkyl, $C_7$–$C_{13}$-aralkyl and $C_6$–$C_{14}$-aryl and the remaining variables are as defined above, and also provides the organometallic compound of the formula IV.

The present invention further provides a process for preparing an organometallic compound of the formula IV by deproteinating one or two carboxylic acid derivatives $R^{16}$—CO—$Nu^1R^1H$ and $R^{17}$—CO—$Nu^2R^2H$ and subsequently reacting the product with an organometallic compound of the formula V

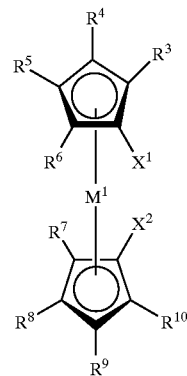

V where $X^1$ and $X^2$ are selected independently from among F, Cl and Br and the remaining variables are as defined above, in the presence of a copper(I) compound and a cosolvent.

The present invention also provides a catalyst system for the polymerization or copolymerization of olefins, comprising one or more organometallic compounds of the formula I and at least one activator, and also a process for the polymerization or copolymerization of olefins using the catalyst system of the present invention. In addition, the present invention provides a solid catalyst comprising an organometallic compound of the formula I, at least one activator and a solid support, and finally provides a process for preparing the solid catalyst of the present invention by impregnation of a support material with one or more organometallic compounds and at least one activator, and a process for the polymerization or copolymerization of olefins in bulk, in suspension or in the gas phase using the solid catalyst of the present invention.

Polymers and copolymers of olefins are of great economic importance because the monomers are readily obtainable in large quantities and because the polymers can be varied within a wide range by variation of the production process or the processing parameters. In the production process, the catalyst used is of particular significance. Apart from Ziegler-Natta catalysts, various single-site catalysts are of increasing importance. As central atoms, not only Zr as in metallocene catalysts ((H.-H. Brintzinger et al., Angew. Chem. 1995, 107, 1255) but also Ni or Pd (WO 96/23010) or Fe and Co (e.g. WO 98/27124) have been examined in detail in recent times.

In the synthesis of catalytically active metallocenes for the polymerization of propylene, there is the problem that most metallocenes are usually obtained as a mixture of the desired racemate form and the unwanted meso form. Suggestions for remedies are known from the literature. Thus, it has been proposed that racemate form and meso form be separated from one another (for example by means of alcoholytic decomposition of the meso isomer as described in DE-A 195 47 247, by complexation with tetramethylethylenediamine "TMEDA" as described in EP-A 0 854 876 and crystallization, or by transformation in a separate step as described in EP-A 0 837 865) or else using specific reaction conditions in the presence of expensive reagents as described in EP-A 0 891 980 (organostannyl reagents). All previously known methods require additional process steps and are therefore costly and disadvantageous.

The use of amido complexes as described in EP-A 0 763 044 is restricted to a few metallocenes which are not relevant to industrial-scale polymerization.

In the search for new catalytically active substances, bis-amide ligands for tetravalent metals of the groups IV to VI of the Periodic Table are of particular interest (G. J. P. Britovsek et al., Angew. Chem. 1999, 111, 448). Their polymerization properties can be controlled within a wide range (cf., for example, N. A. H. Male et al., J. Chem. Commun., Dalton Trans. 1997, 2487; H. Mack et al., J. Organomet. Chem. 1996, 525, 81; C. Averbuj et al., J. Am. Chem. Soc. 1998, 120, 8640; V. C. Gibson et al., J. Chem. Soc., Chem. Commun. 1998, 313). With a view to the polymerization of propylene, an attractive aspect is that they are automatically obtained as racemates in the synthesis and removal of a meso isomer is not necessary. On the other hand, the electronic conditions on the catalytically active center of the bis-amide complexes can be controlled only unsatisfactorily because the substituents which can be introduced on the previously known bis-amide complexes are located far from the catalytically active center.

However, complexes in which the steric and electronic influences of the ligand on the catalytically active center can be controlled in a targeted way are particularly desirable.

Spannenberg et al. (Z. anorg. allg. Chem. 1997, 623, 389) have published ferrocene-containing ligands and their titanium complexes of the formula B,

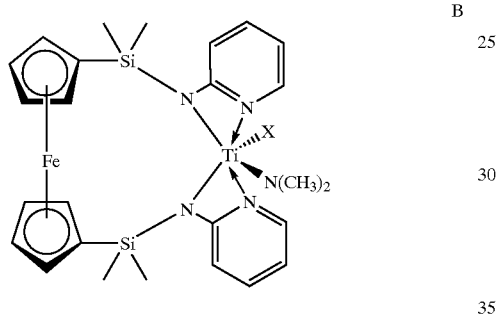

B where X is Cl or $N(CH_3)_2$.

However, complexes of the formula A are unstable and are partially decomposed on heating in hexane. Nothing is known about their activity as polymerization catalysts. They are therefore too sensitive as polymerization catalysts, since most current processes operate at from 60 to 100° C.

It is an object of the present invention
to provide new complexes having, firstly, sufficient thermal stability and, secondly, steric and electronic influences of the ligand on the catalytically active center which can be controlled in a targeted manner,
to provide catalyst systems for the polymerization or copolymerization of olefins from the novel complexes and suitable activators,
to provide a process for the polymerization or copolymerization of olefins using the catalyst systems to be provided,
to provide a process for preparing the complexes to be provided,
to provide a solid catalyst which is suitable for gas-phase polymerization, suspension polymerization or bulk polymerization and comprises a complex of the type to be provided, a suitable activator and a solid support,
to provide a process for preparing a solid catalyst from the novel complexes, and
to provide a process for the polymerization or copolymerization of olefins using the solid catalyst to be provided.

We have found that these objects are achieved by the organometallic compounds defined at the outset.

In formula I, $M^1$ is Fe, Co, Ru or Os, preferably Fe;
$M^2$ is a transition metal of group IV, V or VI of the Periodic Table of the Elements, preferably Ti, Zr, Hf, Cr or V, particularly preferably Ti or Zr;
$Nu^1$ and $Nu^2$ are identical or different and are each selected from among N, P and As; $Nu^1$ and $Nu^2$ are preferably identical and are N or P; $Nu^1$ and $Nu^2$ are particularly preferably both N;
$R^1$ and $R^2$ are identical or different and are selected from among
$C_1$–$C_8$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;
Examples of substituted $C_1$–$C_8$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;
$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl;
Examples of substituted cycloalkyl groups are: 2-methylcyclopentyl, 3-methylcyclopentyl, cis-2,4-dimethylcyclopentyl, trans-2,4-dimethylcyclopentyl, cis-2,5-dimethylcyclopentyl, trans-2,5-dimethylcyclopentyl, 2,2,5,5-tetramethylcyclopentyl, 2-methylcyclohexyl, 3-methylcyclohexyl, 4-methylcyclohexyl, cis-2,6-dimethylcyclohexyl, trans-2,6-dimethylcyclohexyl, cis-2,6-diisopropylcyclohexyl, trans-2,6-diisopropylcyclohexyl, 2,2,6,6-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,6,6-tetrachlorocyclohexyl, 2-thiomethylcyclopentyl, 2-thiomethylcyclohexyl, 3-thiomethylcyclopentyl, 3-thiomethylcyclohexyl and further derivatives;
$C_7$–$C_{13}$-aralkyl, preferably $C_7$–$C_1$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;
$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

$C_6$–$C_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, bearing one or more identical or different substituents selected from among $C_1$–$C_8$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neo-pentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

Examples of substituted $C_1$–$C_8$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

Halogen, for example fluorine, chlorine, bromine or iodine, particularly preferably fluorine or chorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy or 9-anthryloxy;

Silyl groups $SiR^{11}R^{12}R^{13}$, where $R^{11}$ to $R^{13}$ are selected independently from among hydrogen, $C_1$–$C_8$-alkyl groups, benzyl radicals and $C_6$–$C_{14}$-aryl groups; preference is given to the trimethylsilyl, triethylsilyl, triisopropylsilyl, diethylisopropylsilyl, dimethylthexylsilyl, tert-butyldimethylsilyl, tert-butyldiphenylsilyl, tribenzylsilyl, triphenylsilyl and tri-para-xylylsilyl groups; particular preference is given to the trimethylsilyl group and the tert-butyldimethylsilyl group;

Silyloxy groups $OSiR^{11}R^{12}R^{13}$, where $R^{11}$ to $R^{13}$ are selected independently from among hydrogen, $C_1$–$C_8$-alkyl groups, benzyl radicals and $C_6$–$C_{14}$-aryl groups; preference is given to the trimethylsilyloxy, triethylsilyloxy, triisopropylsilyloxy, diethylisopropylsilyloxy, dimethylthexylsilyloxy, tert-butyldimethylsilyloxy, tert-butyldiphenylsilyloxy, tribenzylsilyloxy, triphenylsilyloxy and the tri-para-xylylsilyloxy groups, particular preference is given to the trimethylsilyloxy group and the tert-butyldimethylsilyloxy group;

Very particular preference is given to 2,6-dimethylphenyl, 2,6-diisopropylphenyl, mesityl and 2,6-dichlorophenyl;

five- to six-membered nitrogen-containing heteroaryl radicals such as N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl;

five- to six-membered nitrogen-containing heteroaryl radicals such as N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl bearing one or more identical or different substituents selected from among $C_1$–$C_8$-alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neo-pentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

Examples of substituted $C_1$–$C_8$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

Halogen, for example fluorine, chlorine, bromine or iodine, particularly preferably fluorine or chorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy or 9-anthryloxy;

Silyl groups $SiR^{11}R^{12}R^{13}$, where $R^{11}$ to $R^{13}$ are selected independently from among hydrogen, $C_1$–$C_8$-alkyl groups, benzyl radicals and $C_6$–$C_{14}$-aryl groups; preference is given to the trimethylsilyl, triethylsilyl, triisopropylsilyl, diethylisopropylsilyl, dimethylthexylsilyl, tert-butyldimethylsilyl, tert-butyldiphenylsilyl, tribenzylsilyl, triphenylsilyl and tri-para-xylylsilyl groups; particular preference is given to the trimethylsilyl group and the tert-butyldimethylsilyl group;

Silyloxy groups $OSiR^{11}R^{12}R^{13}$, where $R^{11}$ to $R^{13}$ are selected independently from among hydrogen, $C_1$–$C_8$-alkyl groups, benzyl radicals and $C_6$–$C_{14}$-aryl groups; preference is given to the trimethylsilyloxy, triethylsilyloxy, triisopropylsilyloxy, diethylisopropylsilyloxy, dimethylthexylsilyloxy, tert-butyldimethylsilyloxy, tert-butyldiphenylsilyloxy, tribenzylsilyloxy, triphenylsilyloxy and the tri-para-xylylsilyloxy groups, particular preference is given to the trimethylsilyloxy group and the tert-butyldimethylsilyloxy group;

Very particular preference is given to 2,5-methyl-N-pyrrolyl, 2,5-diisopropyl-N-pyrrolyl and N-carbazolyl.

In a particularly preferred embodiment, $R^1$ and $R^2$ are identical and are selected from among $C_6$–$C_{14}$-aryl, $C_6$–$C_{14}$-aryl bearing one or more identical or different substituents and five- to six-membered nitrogen-containing heteroaryl radicals.

$R^3$ to $R^{10}$ are identical or different and are selected from among hydrogen, $C_1$–$C_8$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

Examples of substituted $C_1$–$C_8$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl;

Examples of substituted cycloalkyl groups are: 2-methylcyclopentyl, 3-methylcyclopentyl, cis-2,4-dimethylcyclopentyl, trans-2,4-dimethylcyclopentyl, cis-2,5-dimethylcyclopentyl, trans-2,5-dimethylcyclopentyl, 2,2,5,5-tetramethylcyclopentyl, 2-methylcyclohexyl, 3-methylcyclohexyl, 4-methylcyclohexyl, cis-2,6-dimethylcyclohexyl, trans-2,6-dimethylcyclohexyl, cis-2,6-diisopropylcyclohexyl, trans-2,6-diisopropylcyclohexyl, 2,2,6,6-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,6,6-tetrachlorocyclohexyl, 2-thiomethylcyclopentyl, 2-thiomethylcyclohexyl, 3-thiomethylcyclopentyl, 3-thiomethylcyclohexyl and further derivatives;

$NO_2$,

Halogen selected from among fluorine, chlorine, bromine and iodine, preferably fluorine or chlorine, $C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

$C_6$–$C_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, bearing one or more identical or different substituents selected from among $C_1$–$C_8$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neo-pentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

Examples of substituted $C_1$–$C_8$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

Halogen, for example fluorine, chlorine, bromine or iodine, particularly preferably fluorine or chorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy or 9-anthryloxy;

Silyl groups $SiR^{11}R^{12}R^{13}$, where $R^{11}$ to $R^{13}$ are selected independently from among hydrogen, $C^1$–$C_8$-alkyl groups, benzyl radicals and $C_6$–$C_{14}$-aryl groups; preference is given to the trimethylsilyl, triethylsilyl, triisopropylsilyl, diethylisopropylsilyl, dimethylthexylsilyl, tert-butyldimethylsilyl, tert-butyldiphenylsilyl, tribenzylsilyl, triphenylsilyl and tri-para-xylylsilyl groups; particular preference is given to the trimethylsilyl group and the tert-butyldimethylsilyl group;

Silyloxy groups $OSiR^{11}R^{12}R^{13}$, where $R^{11}$ to $R^{13}$ are selected independently from among hydrogen, $C_1$–$C_8$-alkyl groups, benzyl radicals and $C_6$–$C_{14}$-aryl groups; preference is given to the trimethylsilyloxy, triethylsilyloxy, triisopropylsilyloxy, diethylisopropylsilyloxy, dimethylthexylsilyloxy, tert-butyldimethylsilyloxy, tert-butyldiphenylsilyloxy, tribenzylsilyloxy, triphenylsilyloxy and the tri-para-xylylsilyloxy groups, particular preference is given to the trimethylsilyloxy group and the tert-butyldimethylsilyloxy group;

Very particular preference is given to 2,6-dimethylphenyl, 2,6-diisopropylphenyl, mesityl and 2,6-dichlorophenyl;

five- to six-membered nitrogen-containing heteroaryl radicals such as N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl;

five- to six-membered nitrogen-containing heteroaryl radicals such as N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl bearing one or more identical or different substituents selected from among $C_1$–$C_8$ alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neo-pentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, sec-butyl and tert-butyl;

Examples of substituted $C_1$–$C_8$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

Halogen, for example fluorine, chlorine, bromine or iodine, particularly preferably fluorine or chorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy and 9-anthryloxy;

Silyl groups $SiR^{11}R^{12}R^{13}$, where $R^{11}$ to $R^{13}$ are selected independently from among hydrogen, $C_1$–$C_8$-alkyl groups, benzyl radicals and $C_6$–$C_{14}$-aryl groups; preference is given to the trimethylsilyl, triethylsilyl, triisopropylsilyl, diethylisopropylsilyl, dimethylthexylsilyl, tert-butyldimethylsilyl, tert-butyldiphenylsilyl, tribenzylsilyl, triphenylsilyl and tri-para-xylylsilyl groups; particular preference is given to the trimethylsilyl group and the tert-butyldimethylsilyl group;

Silyloxy groups $OSiR^{11}R^{12}R^{13}$, where $R^{11}$ to $R^{13}$ are selected independently from among hydrogen, $C_1$–$C_8$-alkyl groups, benzyl radicals and $C_6$–$C_{14}$-aryl groups; preference is given to the trimethylsilyloxy, triethylsilyloxy, triisopropylsilyloxy, diethylisopropylsilyloxy, dimethylthexylsilyloxy, tert-butyldimethylsilyloxy, tert-butyldiphenylsilyloxy, tribenzylsilyloxy, triphenylsilyloxy and the tri-para-xylylsilyloxy groups, particular preference is given to the trimethylsilyloxy group and the tert-butyldimethylsilyloxy group;

Very particular preference is given to 2,5-methyl-N-pyrrolyl, 2,5-diisopropyl-N-pyrrolyl and N-carbazolyl.

$L^1$ to $L^3$ are identical or different and are selected from among $NR^{14}R^{15}$, where $R^{14}$ and $R^{15}$ are identical or different and are selected from among $C_1$–$C_8$ alkyl groups such as methyl, ethyl, n-propyl, isopropyl, n-butyl, isobutyl, sec-butyl, tert-butyl, n-pentyl, isopentyl, sec-pentyl, neopentyl, 1,2- dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neo-pentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl;

$C_2$–$C_8$-alkenyl having one or more conjugated or non-conjugated double bonds, for example, vinyl, allyl, but-2-en-1-yl, but-4-en-1-yl, but-4-en-2-yl, 1,3-butadienyl, pent-2-en-1-yl, 2,2-dime-thyl-pent-1-en-1-yl, 1,3-pentadienyl, ω-hexenyl or ω-octenyl; preferably vinyl, allyl and 1,3-butadienyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

Silyl groups $SiR^{11}R^{12}R^{13}$, where $R^{11}$ to $R^{13}$ are selected independently from among hydrogen, $C_1$–$C_8$-alkyl groups, benzyl radicals and $C_6$–$C_{14}$-aryl groups; preference is given to the trimethylsilyl, triethylsilyl, triisopropylsilyl, diethylisopropylsilyl, dimethylthexylsilyl, tert-butyldimethylsilyl, tert-butyldiphenylsilyl, tribenzylsilyl, triphenylsilyl and tri-para-xylylsilyl groups; particular preference is given to the trimethylsilyl group and the tert-butyldimethylsilyl group;

Silyloxy groups $OSiR^{11}R^{12}R^{13}$, where $R^{11}$ to $R^{13}$ are selected independently from among hydrogen, $C_1$–$C_8$-alkyl groups, benzyl radicals and $C_6$–$C_{14}$-aryl groups; preference is given to the trimethylsilyloxy, triethylsilyloxy, triisopropylsilyloxy, diethylisopropylsilyloxy, dimethylthexylsilyloxy, tert-butyldimethylsilyloxy, tert-butyldiphenylsilyloxy, tribenzylsilyloxy, triphenylsilyloxy and the tri-para-xylylsilyloxy groups, particular preference is given to the trimethylsilyloxy group and the tert-butyldimethylsilyloxy group;

Halide such as fluoride, chloride, bromide and iodide, preferably fluoride and chloride;

$C_1$–$C_8$ alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neo-pentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

Examples of substituted $C_1$–$C_8$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy or 9-anthryloxy, preferably phenoxy.

x is an integer from 0 to 3.

When $L^3$ is selected from among $C_1$–$C_8$-alkyl, $C_3$–$C_{12}$-cycloalkyl, $C_7$–$C_{13}$-aralkyl or $C_6$–$C_{14}$-aryl, then x is preferably 0.

Here, sterically favorably positioned radicals can form a bridge between the two $C_5$ rings, for example $R^5$ and $R^7$ can together be: dimethylsilyl, diphenylsilyl, tetramethyldisilyl, $C_1$–$C_4$-alkylidene which can, for example, be substituted by methyl or phenyl, e.g. methylidene, 2,2-isopropylidene, diphenylmethylene, ethylidene, tetramethylene —($CH_2$)$_4$— or tetramethylethylidene.

Furthermore, in each case two adjacent radicals $R^3$ to $R^6$ or $R^7$ to $R^{10}$ together with the C atoms of the parent aromatic may form a 5- to 8-membered ring which may, if desired, bear further substituents Z. For example, $R^4$ and $R^5$ can together be: —($CH_2$)$_3$— (trimethylene), —($CH_2$)$_4$— (tetramethylene), —($CH_2$)$_5$— (pentamethylene), —($CH_2$)$_6$— (hexamethylene), —$CH_2$—CH=CH—, —$CH_2$—CH=CH—$CH_2$—, —CH=CH—CH=CH—, —O—$CH_2$—O—, —O—CHMe—O—, —CH—($C_6H_5$)—O—, —O—$CH_2$—$CH_2$—O—, —O—C($CH_3$)$_2$—, —$NCH_3$—$CH_2$—$CH_2NCH_3$—, —$NCH_3$—$CH_2$—$NCH_3$— or —O—Si($CH_3$)$_2$—O—.

Z is selected from among $C_1$–$C_8$ alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neo-pentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl, $C_6–C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl.

A very particularly preferred example of compounds of the formula I is the compound of the formula Ia.

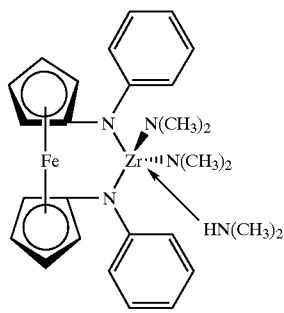

Ia

The novel organometallic compound of the formula I is advantageously prepared by a multistage reaction sequence ending with the reaction of the likewise novel organometallic compound of the formula II with a transition metal compound III.

The starting point of the multistage reaction sequence is a 1,1'-dihalogenmetallocene compound of the formula V which can be prepared from its nonhalogenated derivatives by halogenation of the dilithiated ferrocene using halogens, toluenesulfonide halides or perhalogenated hydrocarbons, as described in R. F. Kovar, M. D. Rausch, H. Rosenberg; Organomet. Chem. Syn. 1970/1971, 1, 173–181.

The novel organometallic compound of the formula II is advantageously prepared by the following reaction sequence:

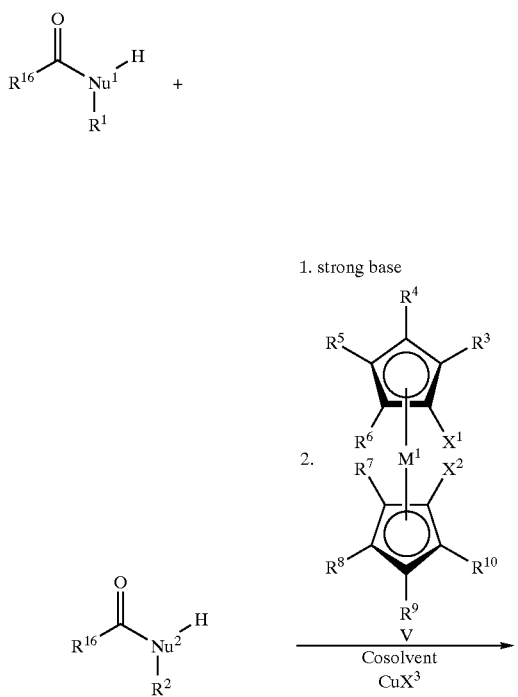

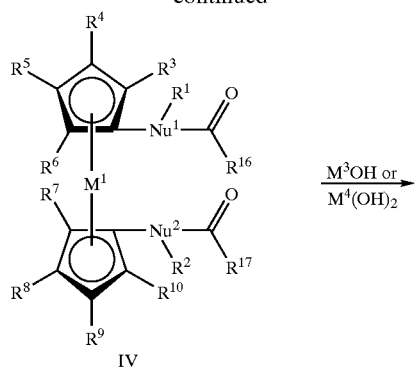

IV

M³OH or M⁴(OH)₂

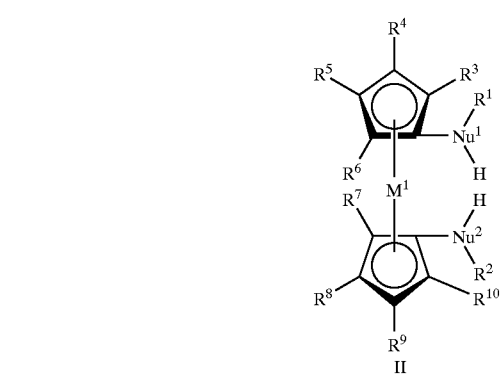

II

In the first step, the two halide ions $(X^1)^-$ and $(X^2)^-$ are replaced by deproteinated carboxylic acid derivatives $R^{16}CONu^1HR^1$ and $R^{17}CONu^2HR^2$ using a procedure based on a method of Herberhold et al., J. Organomet. Chem. 1983, 241, 227.

In the strongly preferred case where $Nu^1$ and $Nu^2$ are identical and $R^1$ and $R^2$ are identical, the first step of the above sequence is carried out using two equivalents of $R^{16}CONu^1HR^1$ instead of one equivalent each of $R^{16}CONu^1HR^1$ and $R^{17}CONU^2HR^2$.

It will be clear to a person skilled in the art that when $Nu^1$ and $Nu^2$ are chosen so as to be different or $R^1$ and $R^2$ are chosen so as to be different, difficult-to-separate product mixtures are generally formed; for this reason, the choice of different $Nu^1$ and $Nu^2$ or/and $R^1$ and $R^2$ is not a preferred embodiment.

$X^1$ to $X^3$ may be identical or different and are selected from among fluorine, chlorine, bromine and iodine, preferably fluorine, chlorine and bromine, particularly preferably chlorine and bromine. $X^1$ and $X^2$ are particularly preferably identical.

The radicals $R^{16}$ and $R^{17}$ are selected from among $C_1–C_8$ alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1–C_6$-alkyl such as methyl, ethyl, n-propyl, isopropyl, n-butyl, isobutyl, sec-butyl, tert-butyl, n-pentyl, isopentyl, sec-pentyl, neo-pentyl, 1,2-dimethylpropyl, isoamyl, n-hexyl, isohexyl, sec-hexyl, particularly preferably $C_1–C_2$-alkyl such as methyl or ethyl and very particularly preferably methyl;

$C_3–C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl.

$R^{16}$ and $R^{17}$ may be identical or different; they are preferably identical.

In the first step of the reaction sequence, the carboxylic acid derivatives or derivatives is/are deproteinated by means of a strong base. Examples of suitable strong bases are: lithium amide, sodium amide, potassium amide, potassium hydride and lithium diisopropylamide ("LDA"). Solvents which have been found to be useful are high-boiling solvents such as toluene, ortho-xylene meta-xylene, para-xylene, ethylbenzene and mixtures thereof.

This reaction is generally complete after a few hours; a reaction time of from 2 to 10 hours is appropriate. A time of from 3 to 5 hours is preferred. The reaction temperatures are generally not critical; a temperature above 100° C. has been found to be useful.

As cosolvent, it is possible to use compounds which are known as uncharged ligands in coordination chemistry, for example pyridine, lutidine, collidine, dimethyl sulfide or triphenylphosphine, preferably pyridine. As solvents, high-boiling solvents such as toluene, ortho-xylene, meta-xylene, para-xylene, ethylbenzene or mixtures thereof have been found to be useful.

Catalysts employed for this reaction are salts of monovalent copper, preferably CuCl or CuBr, with from 5 mol % to 150 mol % based on the carboxylic acid derivative or derivatives having been found to be advantageous.

This reaction is brought about by heating for a number of hours. A period of from 2 to 100 hours has been found to be useful; preference is given to from 5 to 96 hours and particular preference is given to from 48 to 75 hours. The reaction temperatures are important in this case; a temperature above 100° C. has been found to be advantageous and boiling under reflux is particularly preferred. Shorter reaction times or lower temperatures usually, but not always, lead to incomplete reaction.

After this step, the product is advantageously purified by crystallization or chromatography. Removal of impurities by extraction has also been found to be a useful method of work-up.

The elimination of the carbonyl groups can be carried out under various reaction conditions. Examples which may be mentioned are: saponification under alkaline conditions using $M^3OH$ or $M^4(OH)_2$ or acid hydrolysis in the presence of catalytic amounts of, for example, sulfuric acid or phosphoric acid.

Here, $M^3$ is selected from among Li, Na, K, Rb and Cs, preferably Na and K;

$M^4$ is selected from among Mg, Ca, Sr and Ba, and is preferably Ca.

Preference is given to saponification under alkaline conditions. The reaction is advantageously carried out using an excess of hydroxide $M^3OH$ or $M^4(OH)_2$ in a relatively high-boiling alcohol, for example ethanol, n-propanol, n-butanol, glycol or 1,3-propanediol. The alcohol can, if desired, be mixed with from 0.1 to 50% by volume of water. The hydroxide excess is in the range from 10 mol % to 100,000 mol %. It is usually necessary to heat the saponification mixture for from 2 to 48 hours, preferably from 8 to 24 hours.

After the reaction, the organometallic compound of the formula II generally has to be purified, which is carried out by means of chromatography, crystallization, extraction or other typical work-up steps of organic synthesis. The removal of moisture and traces of hydroxides from the product is particularly important.

The novel organometallic compounds of the formula I are prepared by reacting an organometallic compound of the formula II with a transition metal compound of the formula III, where the variables in the formulae II and III are as defined above. The conditions for the reaction are not critical per se; the usual procedure is to mix II and III with one another in a suitable solvent such as benzene, toluene, ethylbenzene, ortho-xylene, meta-xylene or para-xylene, chlorobenzene, cyclohexane, methylene chloride or a mixture thereof. A suitable temperature range is from –100° C. to +150° C., preferably from –78° C. to +100° C. The reaction temperature should not be below the melting point of the solvent; in addition, temperatures above the boiling point of the solvent concerned can only be achieved in autoclave reactions and are less preferred. However, it is important that the reaction be carried out in the absence of oxygen and moisture.

Suitable molar ratios of II:III are in the range from 5:1 to 1:5. However, since the transition metal compounds of the formula II are the reactants which are more difficult to obtain, preference is given to molar ratios of II:III in the range from 1:1 to 1:3. Particular preference is given to stoichiometric amounts.

The purification of the novel organometallic compounds of the formula I is carried out by the methods customary in organometallic chemistry, with crystallization being particularly preferred. Filtration through filter aids such as Celite® is also useful.

The preparation of transition metal compounds of the formula III is described by way of example in G. M. Diamond et al., Organometallics 1996, 15, 4030.

Organometallic compounds of the formula I can easily be oxidized when $M^1$ is selected from among Fe and Co. Oxidants which have been found to be useful are $HNO_3$ and $C_1$–$C_8$-alkyl halides; electrochemical methods are also suitable. Further examples of useful oxidants are $NOBF_4$ and suitable ferrocenium salts and silver(I) salts such as $AgNO_3$, $AgBF_4$ or $Ag_2C_2O_4$ (silver oxalate). Oxidation or partial oxidation, i.e. not stoichiometric oxidation, makes it possible to achieve a fine adjustment in the electron density on the catalytically active central atom $M^2$. When the use of organometallic compounds of the formula I as catalysts is referred to, this includes the fully or partially oxidized derivatives.

Partially oxidized derivatives are suitable for preparing polymers having a bimodal molecular weight distribution.

For the organometallic compounds of the formula I to be polymerization-active, they have to be activated by means of a cocatalyst. Suitable cocatalysts are aluminum alkyls of the formula $AlR_3$, lithium alkyls of the formula LiR and aluminoxanes, with particular preference being given to aluminoxanes.

In these cocatalysts, the radicals R are identical or different and are $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl or n-dodecyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl or tert-butyl.

The structure of the aluminoxanes is not precisely known. These compounds are products which are obtained by careful partial hydrolysis of aluminum alkyls (cf. DE-A 30 07 725). These products are not uniform compounds, but are mixtures of open-chain and cyclic structures of the types VIa and b.

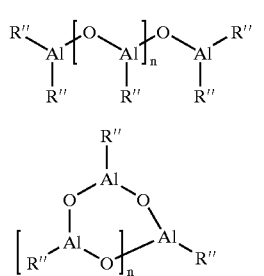

VIa

VIb

In the formulae VIa and VIb, the radicals R" are identical or different and are, independently of one another, $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl, or n-dodecyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably methyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl or cyclododecyl; preference is given to cyclopentyl, cyclohexyl and cycloheptyl;

$C_7$–$C_{20}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, or $C_6$–$C_{14}$-aryl such asphenyl, 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl, preferably phenyl, 1-naphthyl and 2-naphthyl, particularly preferably phenyl; and n is an integer from 0 to 40, preferably from 0 to 25 and particularly preferably from 0 to 22.

In the literature, cage-like structures are also discussed for aluminoxanes (Y. Koide, S. G. Bott, A. R. Barron Organometallics 1996, 15, 2213–26; A. R. Barron Macromol. Symp. 1995, 97, 15). Regardless of the actual structure of the aluminoxanes, they are useful as scavenger alkyls and as cocatalysts for the novel organometallic compounds of the formula I.

Activating the inventive organometallic compounds of the formula I with aluminoxanes generally requires an excess of aluminoxane over M. Rational molar ratios M:Al lie in the range from 1:10 to 1:10 000, preferably 1:50 to 1:1 000, and, with particular preference, 1:100 to 1:500.

Another class of suitable cocatalysts is made up of strong Lewis acids and salts of noncoordinating or only weakly coordinating anions bearing bulky substituents. Suitable Lewis acids and salts are selected boron compounds having electron-withdrawing groups (e.g. trispentafluorophenylborane, N,N-dimethylanilinium tetrakispentafluorophenylborate, tri-n-butylammonium tetrakispentafluorophenylborate, N,N-dimethylanilinium tetrakis(3,5-bisperfluoromethyl)phenylborate, tri-n-butylammonium tetrakis(3,5-bisperfluoromethyl) phenylborate and tritylium tetrakispentafluorophenylborate). These activators are disclosed in EP-A 0 468 537 and EP-A 0 426 638. Preference is given to dimethylanilinium tetrakispentafluorophenylborate, tritylium tetrakispentafluorophenylborate and trispentafluorophenylborane (X. Yang et al., *J. Am. Chem. Soc.* 1991, 113, 3623). These activators are usually used together with an aluminum alkyl compound for activating the novel organometallic compound of the formula I.

Where boron or aluminum compounds are used as activators for the inventive organometallic compounds of the formula I, they are generally employed in a molar ratio of from 1:10 to 10:1, based on M, preferably 1:2 to 5:1 and with particular preference 1:2 to 2:1 and with very particular preference 1:1.

It is also possible to use mixtures of two or more aluminum alkyls or lithium alkyls as cocatalyst and scavenger alkyl. Mixtures of aluminum alkyls with lithium alkyls are also suitable.

Pressure and temperature conditions during the polymerization can be selected within wide limits. A pressure range from 0.5 bar to 4000 bar has been found to be suitable; preference is given to from 10 to 75 bar or high-pressure conditions from 500 to 2500 bar. A suitable temperature range has been found to be from 0 to 120° C.; preference is given to from 40 to 100° C. and particular preference to from 50 to 85° C.

Suitable monomers are the following olefins: ethylene, propylene, 1-butene, 1-pentene, 1-hexene, 1-octene, 1-decene and 1-undecene, with ethylene being particularly preferred.

Suitable comonomers are a-olefins, for example from 0.1 to 20 mol % of 1-butene, 1-pentene, 1-hexene, 4-methyl-1-pentene, 1-octene, 1-decene or 1-undecene. However, isobutene and styrene are also suitable comonomers.

Solvents which have been found to be useful are toluene, ortho-xylene, meta-xylene, para-xylene and ethylbenzene and mixtures thereof. A further possible solvent is, under high-pressure conditions, supercritical ethylene.

If the use of aluminum alkyl or lithium alkyl as scavenger alkyl is found to be necessary, it is advantageous to meter-in the aluminum alkyl or lithium alkyl as a solution in a hydrocarbon separately from the catalyst system. However, the scavenger alkyl can also be metered-in together with the novel organometallic compound I.

The catalyst system of the present invention has also been found to be regulatable by means of hydrogen, i.e. the molecular weight of the polymers obtainable by means of the catalyst system of the present invention can be reduced by addition of hydrogen. If sufficient hydrogen is added, waxes are obtained. The hydrogen concentration required depends, inter alia, on the type of polymerization plant employed.

The novel organometallic compounds of the formula I can also be used together with metallocenes for catalyzing the polymerization of olefins. For this purpose, they can be activated together with or separately from the metallocenes and also introduced into the polymerization system either together or separately.

For the organometallic compounds of the formula I to be able to be used in modern polymerization processes such as suspension processes, bulk polymerization processes or gas-phase processes, they have to be immobilized on a solid support. Otherwise, polymer morphology problems (lumps, deposits on the walls, blockages in lines or heat exchangers) can occur and force a shutdown of the plant. Such an immobilized organometallic compound of the formula I is referred to as a catalyst.

It has been found that organometallic compounds of the formula I can readily be deposited on a solid support. Suitable support materials are, for example, porous metal oxides of metals of groups 2–14 or mixtures thereof, also sheet silicates and zeolites. Preferred examples of metal oxides of elements of groups 2–14 are $SiO_2$, $B_2O_3$, $Al_2O_3$, MgO, CaO and ZnO. Preferred sheet silicates are montmorillonites and bentonites; the preferred zeolite is MCM-41.

Particularly preferred support materials are spherical silica gels and aluminosilicate gels of the formula $SiO_2 \cdot a\ Al_2O_3$, where a is generally from 0 to 2, preferably from 0 to 0.5. Such silica gels are commercially available, e.g. Silica Gel SG 332, Sylopol® 948 or 952 or S 2101 from W. R. Grace or ES 70X from Crosfield.

As particle size of the support material, mean particle diameters of from 1 to 300 μm have been found to be useful; preference is given to particle diameters of from 20 to 80 μm. These particle diameters are determined by known methods such as sieve methods. The pore volume of these supports is from 1.0 to 3.0 ml/g, preferably from 1.6 to 2.2 ml/g and particularly preferably from 1.7 to 1.9 ml/g. The BET surface area is from 200 to 750 m²/g, preferably from 250 to 400 m²/g.

To remove impurities, particularly moisture, adhering to the support material, the support materials can be baked out before doping, with temperatures of from 45 to 1000° C. being suitable. Temperature of from 100 to 750° C. are particularly suitable for silica gels and other metal oxides. This baking-out should be carried out for a period of from 0.5 to 24 hours, preferably from 1 to 12 hours. The pressure conditions depend on the method selected; baking-out can be carried out in a fixed bed, in a stirred vessel or else in a fluidized bed. Baking-out can quite generally be carried out at atmospheric pressure. However, reduced pressures of from 0.1 to 500 mbar are advantageous; a range from 1 to 100 mbar is particularly advantageous and a range from 2 to 20 mbar is very particularly advantageous. On the other hand, in fluidized-bed methods, it is advisable to employ slightly elevated pressure, for example from 1.01 bar to 5 bar, preferably from 1.1 to 1.5 bar.

Chemical pretreatment of the support material with an alkyl compound such as an aluminum alkyl $AlR_3$, a lithium alkyl LiR or an aluminoxane of the formulae VIa and VIb is also possible.

For polymerization in a suspension process, use is made of suspension media in which the desired polymer is insoluble or only slightly soluble, since otherwise deposits of product are formed in the parts of the plant in which the product is separated from the suspension medium and these force repeated shutdowns and cleaning operations. Suitable suspension media are saturated hydrocarbons such as propane, n-butane, isobutane, n-pentane, isopentane, n-hexane, isohexane and cyclohexane, with isobutane being preferred.

Pressure and temperature conditions during the polymerization can be selected within wide limits. A pressure range from 0.5 bar to 150 bar has been found to be useful; preference is given to a pressure in the range from 10 to 75 bar. A temperature range of from 0 to 120° C. has been found to be useful; preference is given to a range from 40 to 100° C., particularly preferably from 50 to 85° C.

Suitable monomers are the following olefins: ethylene, propylene, 1-butene, 1-pentene, 1-hexene, 1-octene, 1-decene or 1-undecene.

Suitable comonomers are α-olefins for example from 0.1 to 20 mol % of 1-butene, 1-pentene, 1-hexene, 4-methyl-1-pentene, 1-octene, 1-decene or 1-undecene. Isobutene and styrene are also suitable comonomers.

Hydrogen has been found to be an efficient chain transfer reagent for the catalysts of the present invention, i.e. the molecular weight of the polymers obtainable by means of the catalysts of the present invention can be reduced by addition of hydrogen. If sufficient hydrogen is added, waxes are obtained. The hydrogen concentration required depends, inter alia, on the type of polymerization plant employed. It has also been observed that the activity of the catalysts of the present invention increases when hydrogen is added.

The catalysts of the present invention can also be used together with one or more other polymerization catalysts known per se. Thus, they can be used together with Ziegler-Natta catalysts, supported metallocene catalysts of transition metals of groups IV to VI of the Periodic Table of the Elements, Catalysts derived from late transition metals (WO 96/23010), Fe or Co complexes with pyridyldiimine ligands, as are disclosed in WO 98/27124 or chromium oxide catalysts of the Phillips type.

Here, various catalysts can be mixed with one another and be introduced together or cosupported complexes on a common support can be used, or various catalysts can be metered separately into the polymerization vessel at the same point or at different points.

EXAMPLE

1. Preparation of 1,1'-bis(N-phenyl-N-acetamido)ferrocene 0.25 g (1.8 mmol) of N-phenylacetamide in 30 ml of absolute toluene were heated under argon with 0.087 g (2.2 mmol) of sodium amide for one hour under reflux. After cooling, the solvent was taken off in a high vacuum, the white residue was redissolved in 30 ml of toluene and subsequently heated with 0.3 g (2.1 mmol) of copper(I) bromide, 0.3 g (0.87 mmol) of 1,1'-dibromoferrocene and 0.5 ml of pyridine (absolute) for 72 hours under reflux. The toluene was taken off on a rotary evaporator, the residue was carefully dried and subsequently purified by column chromatography (Alox, eluant: methylene chloride/acetonitrile).

Yield: 0.271 g (0.60 mmol, 68%).

Data: yellow powder, $C_{26}H_{24}FeN_2O_2$, M=452.33 g/mol, m.p.: 124° C. MS (EI): 452 (M$^+$, 100%), 410 (M$^+$—$CH_3O$, 4%), 254 (M$^+$—$CpNPhCOCH_3$, 58%). IR (KBr): 3085w, 3069w, 1672s, 1593m, 1493s, 1464s, 1410w, 1368m, 1327m, 1314m, 1281w, 1225w, 1032m, 1014w, 852m, 806m, 771w, 764m, 700s, 636w, 600m, 526w, 478m, 457w cm$^{-1}$. $^1$H-NMR (CDCl$_3$): 1.82 (6H, s, CH$_3$); 3.89 (4H, m, Cp$_{subst}$); 4.32 (4H, m, Cp$_{subst}$); 7.32–7.48 (10H, m, phenyl). $^{13}$C-NMR (CDCl$_3$): 24.7 (CH$_3$); 63.2, 65.9, 102.2 (ferrocene); 128.3, 128.8, 129.7, 142.5 (phenyl); 169.6 (C=O).

2. Preparation of 1,1'-bis(phenylamino)ferrocene 0.248 g (0.55 mmol) of 1,1'-bis(phenylacetamido)ferrocene in 30 ml of argon-saturated ethanol (96%) were heated under argon with 2 g (35.6 mmol) of potassium hydroxide for 16 hours under reflux. After cooling, the reaction mixture was (without inert gas) diluted with 30 ml of argon-saturated water, transferred to a separating funnel and extracted a number of times with ether. The combined ether phases were dried over sodium sulfate, filtered and evaporated under argon in a high vacuum.

Yield: 0.147 g (0.40 mmol, 73%).

Data: a yellow air-sensitive powder, $C_{22}H_{20}FeN_2$, M=368.26 g/mol. $^1$H-NMR (CDCl$_3$): 3.99 (4H, m, Cp$_{subst}$); 4.22 (4H, m, Cp$_{subst}$); 6.74–7.16 (10H, m, phenyl). $^{13}$C-NMR (CDCl$_3$): 62.6, 64.8, 99.6 (ferrocene); 114.3, 118.4, 128.8, 145.7 (phenyl).

3. Preparation of

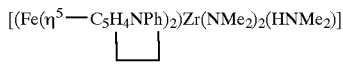
(Ia)

7 ml of benzene are added to 630.0 mg (2.35 mmol) of Zr(NMe$_2$)$_4$ and 867.2 mg (2.35 mmol) of 1,1'-bis (phenylamino)ferrocene. A light-yellow solid immediately precipitates from the reaction solution. The reaction mixture is stirred at room temperature for 1 hour. The product is subsequently recrystallized from benzene. This gives 0.99 g (1.68 mmol, 71%) of Ia as analytically pure yellow crystals.

$\delta_H$(CDCl$_3$, 298 K) 2.39 (br s, 6H, HNMe$_2$), 3.05 (s, 12H, NMe$_2$), 3.70 (t, 4H, $^3J_{HH}$=1.9, cyclopentadienyl), 4.62 (t, 4H, $^3J_{HH}$=1.9, cyclopentadienyl), 6.66 (t, $^3J_{HH}$=7.2, 2H, p-aryl H), 6.74 (d, 4H, $^3J_{HH}$=7.8, o-aryl H), 7.17 (t, 4H, $^3J_{HH}$=7.7, m-aryl H); $\delta_c$(CDCl$_3$, 298 K) 39.1, 43.2, 68.5, 70.5, 89.9, 115.3, 117.0, 129.1, 153.9

4. Preparation of

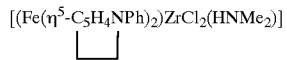
(Ib)

277.0 mg (0.47 mmol) of Ia and 76.6 mg (0.94 mmol) of HNMe$_2$.HCl are admixed with 5 ml of benzene. This gives a clear orange solution. The reaction solution is stirred at room temperature for 15 hours. The resulting yellow solid is filtered off and recrystallized from chloroform. This gives 91.7 mg (0.16 mmol, 33%) of Ib as an analytically pure yellow solid.

$\delta_c$(CDCl$_3$, 298 K) 40.4, 68.1, 70.9, 72.7, 73.8, 81.6, 116.2, 120.3, 128.9, 151.5

5. Polymerization Example 450 ml of toluene were placed in a 1 l steel autoclave from Büchi. A mixture of 2 ml of methylaluminoxane (30% strength by weight solution in toluene, from Witco) and 20 mg of the complex Ia was added thereto. The autoclave was heated to 70° C. and pressurized with ethylene to a pressure of 40 bar. The ethylene pressure was kept constant by automatic metering-in of further amounts. After 90 minutes, the polymerization was stopped by venting the autoclave. 13.1 g of polyethylene were isolated as a white powder, which corresponds to an activity of 260 kg of PE/mol.h. The polymer viscosity, determined in accordance with ISO 1628-3, was 0.3 dl/g.

We claim:

1. An organometallic compound of the formula I,

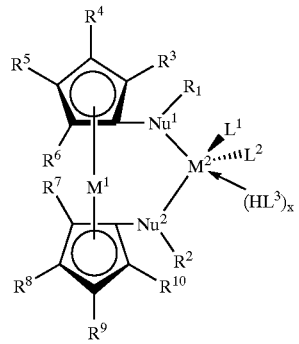

I where the variables are defined as follows:

$M^1$ is selected from among Fe, Co, Ru and Os, $M^2$ is a transition metal of group 4, 5 or 6 of the Periodic Table of the Elements, $Nu^1$ and $Nu^2$ are identical or different and are selected from among N, P and As, $R^1$ and $R^2$ are identical or different and are selected from among $C_1$–$C_8$-alkyl, substituted or unsubstituted, $C_3$–$C_{12}$-cycloalkyl, substituted or unsubstituted, $C_7$–$C_{13}$-aralkyl, $C_6$–$C_{14}$-aryl, unsubstituted or substituted by one or more identical or different substituents selected from among $C_1$–$C_8$-alkyl, substituted or unsubstituted, $C_3$–$C_{12}$-cycloalkyl, $C_7$–$C_{13}$-aralkyl, $C_6$–$C_{14}$-aryl, halogen, $C_1$–$C_6$-alkoxy, $C_6$–$C_{14}$-aryloxy, $SiR^{11}R^{12}R^{13}$ and O—$SiR^{11}R^{12}R^{13}$ where $R^{11}$–$R^{13}$ are selected from among $C_1$–$C_8$-alkyl, $C_3$–$C_{12}$-cycloalkyl, $C_7$–$C_{13}$-aralkyl or $C_6$–$C_{14}$-aryl;

five- to six-membered nitrogen-containing heteroaryl radicals, unsubstituted or substituted by one or more identical or different substituents selected from among $C_1$–$C_8$-alkyl, substituted or unsubstituted, $C_3$–$C_{12}$-cycloalkyl, $C_7$–$C_{13}$-aralkyl, $C_6$–$C_{14}$-aryl, halogen, $C_1$–$C_6$-alkoxy, $C_6$–$C_{14}$-aryloxy, $SiR^{11}R^{12}R^{13}$ and O—$SiR^{11}R^{12}R^{13}$, where $R^{11}$–$R^{13}$ are selected from among $C_1$–$C_8$-alkyl, $C_3$–$C_{12}$-cycloalkyl, $C_7$–$C_{13}$-aralkyl or $C_6$–$C_{14}$-aryl;

$R^3$ to $R^{10}$ are hydrogen, $C_1$–$C_8$-alkyl, substituted or unsubstituted, $C_3$–$C_{12}$-cycloalkyl, substituted or unsubstituted, $NO_2$, halogen, $C_7$–$C_{13}$-aralkyl, $C_6$–$C_{14}$-aryl, unsubstituted or substituted by one or more identical or different substituents selected from among $C_1$–$C_8$-alkyl, substituted or unsubstituted,
$C_3$–$C_{12}$-cycloalkyl,
$C_7$–$C_{13}$-aralkyl,
$C_6$–$C_{14}$-aryl,
halogen,
$C_1$–$C_6$-alkoxy,
$C_6$–$C_{14}$-aryloxy,
$SiR^{11}R^{12}R^{13}$ and $O{-}SiR^{11}R^{12}R^{13}$, where $R^{11}$–$R^{13}$ are selected from among $C_1$–$C_8$-alkyl, $C_3$–$C_{12}$-cycloalkyl, $C_7$–$C_{13}$-aralkyl or $C_6$–$C_{14}$-aryl;

five- to six-membered nitrogen-containing heteroaryl radicals, unsubstituted or substituted by one or more identical or different substituents selected from among $C_1$–$C_8$-alkyl, substituted or unsubstituted,
$C_3$–$C_{12}$-cycloalkyl,
$C_7$–$C_{13}$-aralkyl,
$C_6$–$C_{14}$-aryl,
halogen,
$C_1$–$C_6$-alkoxy,
$C_6$–$C_{14}$-aryloxy,
$SiR^{11}R^{12}R^{13}$ or $O{-}SiR^{11}R^{12}R^{13}$, where $R^{11}$–$R^{13}$ are selected from among $C_1$–$C_8$-alkyl, $C_3$–$C_{12}$-cycloalkyl, $C_7$–$C_{13}$-aralkyl or $C_6$–$C_{14}$-aryl;

where in each case two adjacent radicals $R^3$ to $R^6$ or $R^7$ to $R^{10}$ together with the C atoms of the parent aromatic may form a 5- to 8-membered ring or sterically favorably positioned radicals may form a bridge between the two $C_5$ rings;

$L^1$ to $L^3$ are identical or different and are selected from among $NR^{14}R^{15}$, where $R^{14}$ and $R^{15}$ are identical or different and are selected from among $C_1$–$C_8$-alkyl, $C_3$–$C_{12}$-cycloalkyl, $C_2$–$C_8$-alkenyl having one or more conjugated or nonconjugated double bonds, $C_7$–$C_{13}$-aralkyl, $C_6$–$C_{14}$-aryl, $SiR^{11}R^{12}R^{13}$ and $O{-}SiR^{11}R^{12}R^{13}$, where $R^{11}$–$R^{13}$ are selected from among $C_1$–$C_8$-alkyl, $C_3$–$C_{12}$-cycloalkyl, $C_7$–$C_{13}$-aralkyl and $C_6$–$C_{14}$-aryl; and where $R^{14}$ and $R^{15}$ together with N may form a five- to ten-membered, saturated or unsaturated ring which may in turn be substituted by $C_1$–$C_6$-alkyl, halide,
$C_1$–$C_8$-alkyl, substituted or unsubstituted,
$C_3$–$C_{12}$-cycloalkyl,
$C_7$–$C_{13}$-aralkyl,
$C_6$–$C_{14}$-aryl,
$C_1$–$C_6$-alkoxy;
$C_6$–$C_{14}$-aryloxy, x is an integer from 0 to 3.

2. An organometallic compound of the formula I in which $Nu^1$ and $Nu^2$ are each N and $R^1$ and $R^2$ are identical and are selected from among unsubstituted $C_6$–$C_{14}$-aryl, $C_6$–$C_{14}$-aryl bearing one or more identical or different substituents and five- to six-membered nitrogen-containing heteroaryl radicals.

3. A process for preparing an organometallic compound of the formula I, which comprises reacting an organometallic compound of the formula II

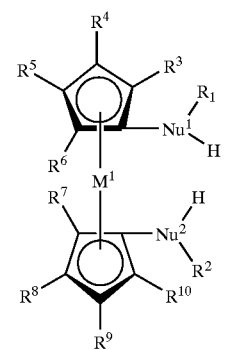

II with a transition metal compound of the formula III $$M^2L^1L^2(L^3)_{x+1} \qquad \text{III}$$

where the variables are as defined above.

4. A process as claimed in claim 3, wherein the organometallic compound of the formula II is firstly doubly deproteinated by means of a base.

5. A catalyst composition, comprising one or more of the organometallic compounds of formula I defined in claim 1, at least one activator, and optionally a solid support.

6. A process for the polymerization or copolymerization of olefins which comprises polymerizing or copolymerizing the olefins in the presence of the catalyst composition defined in claim 5.

7. The process of claim 6, wherein the polymerization or copolymerization is conducted in bulk, in suspension or in the gas phase.

* * * * *

UNITED STATES PATENT AND TRADEMARK OFFICE
CERTIFICATE OF CORRECTION

PATENT NO. : 6,743,932 B2  Page 1 of 1
DATED : June 1, 2004
INVENTOR(S) : Kristen et al.

It is certified that error appears in the above-identified patent and that said Letters Patent is hereby corrected as shown below:

<u>Column 26,</u>
Line 36, "is firstly doubly deproteinated" should read -- is firstly deproteinated --.

Signed and Sealed this

Twenty-second Day of March, 2005

JON W. DUDAS
*Director of the United States Patent and Trademark Office*